United States Patent [19]

Sullivan

[11] Patent Number: 5,017,187

[45] Date of Patent: May 21, 1991

[54] SELF RETRACTING HYPODERMIC SYRINGE

[76] Inventor: Robert J. Sullivan, 15 Floramar, Rancho Santa Margarita, Calif. 62688

[21] Appl. No.: 519,281

[22] Filed: May 4, 1990

[51] Int. Cl.⁵ .............................................. A61M 5/00
[52] U.S. Cl. ..................... 604/110; 604/192
[58] Field of Search ............... 604/110, 134, 135, 192, 604/195, 198, 218, 228

[56] References Cited

U.S. PATENT DOCUMENTS

| | | | |
|---|---|---|---|
| 4,747,831 | 5/1988 | Kulli | 604/110 |
| 4,772,265 | 9/1988 | Walter | 604/164 |
| 4,795,432 | 1/1989 | Karczmer | 604/110 |
| 4,795,443 | 1/1989 | Parmenter et al. | 604/198 |
| 4,804,371 | 2/1989 | Vaillancourt | 604/198 |
| 4,820,275 | 4/1989 | Haber et al. | 604/198 |
| 4,828,548 | 5/1989 | Walter | 604/164 |
| 4,838,869 | 6/1989 | Allard | 604/195 |
| 4,911,693 | 3/1990 | Paris | 604/192 |
| 4,921,486 | 5/1990 | De Chellis et al. | 604/110 |
| 4,931,040 | 6/1990 | Haber et al. | 604/110 |
| 4,966,593 | 10/1990 | Lennox | 604/110 |
| 4,973,316 | 11/1990 | Dysarz | 604/110 |
| 4,978,343 | 12/1990 | Dysanz et al. | 604/110 |

FOREIGN PATENT DOCUMENTS 0347742  12/1989  European Pat. Off. ............ 604/110

Primary Examiner—C. Fred Rosenbaum
Assistant Examiner—Sharon Rose

[57] ABSTRACT

A self retracting hypodermic syringe resembles and is used like a standard syringe except that it is automatically disabled at the instant that the injection is completed. During the injection, the plunger is pressed into the syringe body. When the plunger reaches the front of the syringe an actuating element attaches to the needle assembly and unlocks it from the syringe body. At the same time a spring is unlatched driving the injection needle into the body of the syringe. In order to actuate the spring the plunger must be driven beyond a detent provided for tactile identification of the limit of travel for the purpose of filling the syringe. After use, the needle cannot be retrieved and the syringe is not reusable. The fast withdrawal of the needle from the patient results in much less pain.

4 Claims, 3 Drawing Sheets

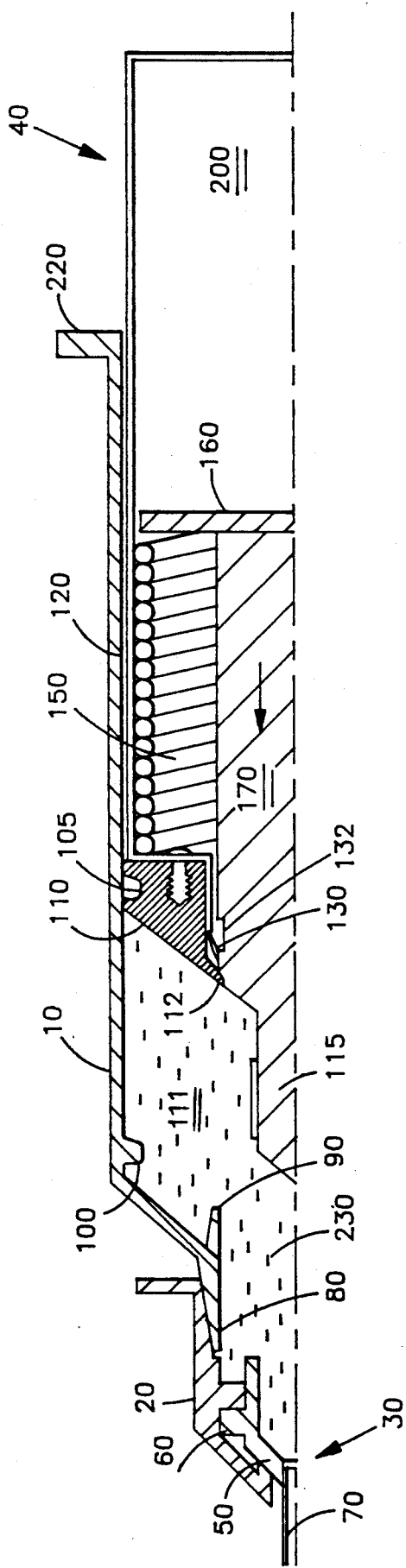
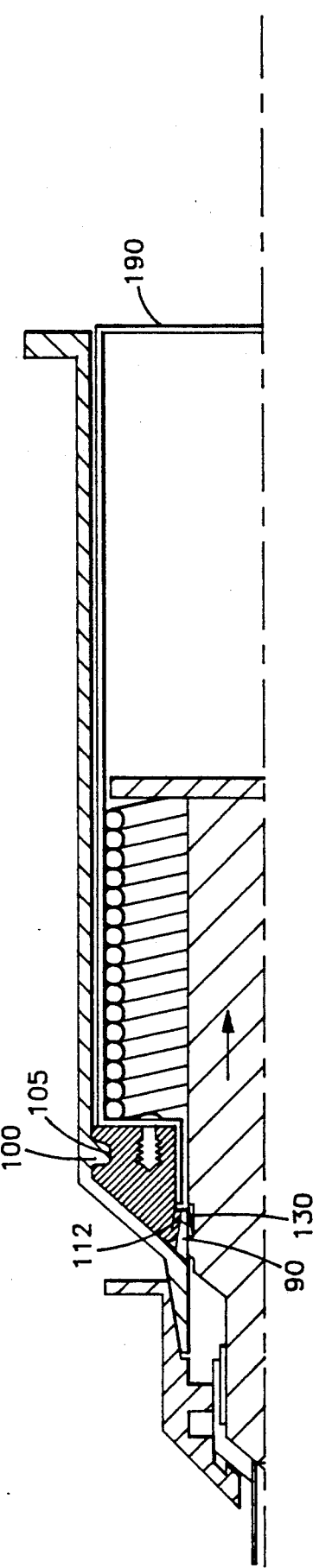
FIG. 2
FIG. 3

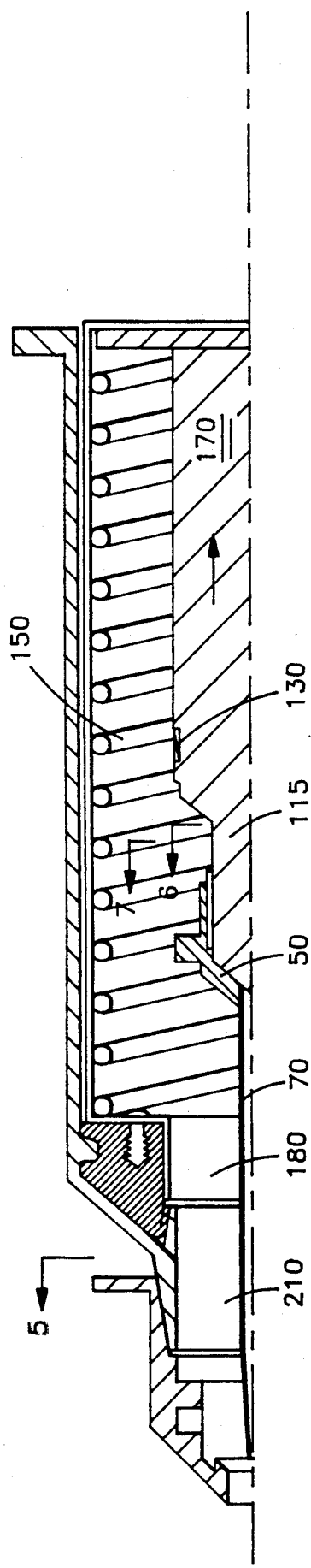
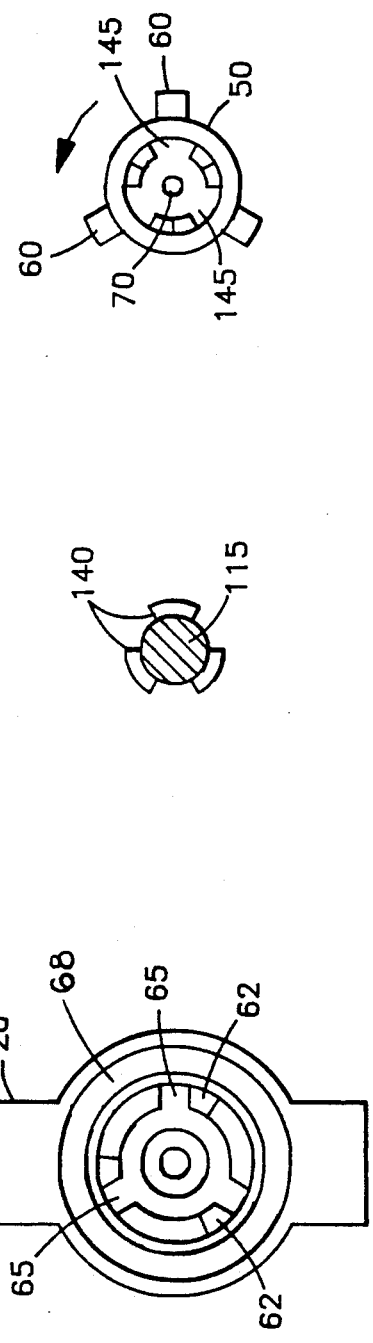
FIG. 4
FIG. 6
FIG. 7
FIG. 5

SELF RETRACTING HYPODERMIC SYRINGE

BACKGROUND OF THE INVENTION

The invention relates in general to hypodermic syringes for medical injection and more particularly to syringes which are limited to a single use, thereby preventing the spread of disease by drug offenders, and others, through the sharing of syringes. The invention relates also to devices for the protection of medical workers, and others, from accidental syringe needle scratches.

DESCRIPTION OF THE PRIOR ART

U.S. Pat. Nos. 4,772,265 and 4,828,548 Walter both teach an apparatus for the safe disposal of a medical needle after use. Both vacuum and springs are used to retract the needle into a sheath after use. U.S. Pat. No. 4,820,275 to Haber et al describes a dental syringe utilizing a double cylinder with spring action for retracting the needle after use. U.S. Pat. No. 4,804,371 to Vaillancourt describes a series of embodiments which utilize springs, accordion pleats and other means to urge a sheath forward to cover the tip of a needle after use. U.S. Pat. No. 4,795,443 to Permenter teaches a device for sealing the tip of a needle after use. The device is stored on the syringe barrel until needed and is then forced forward into position for use. U.S. Pat. No. 4,795,432 to Karczmer provides for an automatic shield assembly which is actuated by needle use and which protrudes forward to cover the needle after use. The prior art does not teach a device which provides automatic retraction of the needle at the completion of the injection cycle and which is then rendered nonreuseable. There is a need for such a device. Cases of the spread of AIDS to medical workers have been reported due to accidental scratches after the injection of an AIDS patient. No matter how careful a worker may be, there is always the possibility of accident if the decision for needle retraction, covering or disposal requires a conscious decision. The present invention provides a device which takes that decision away from medical personnel.

SUMMARY OF THE INVENTION AND OBJECTS

A self retracting hypodermic syringe has a tubular body, a separable injection needle supported at one end and a plunger assembly inserted from the opposite end. The plunger assembly is sealed against the inner surface of the syringe by an annular sealing ring so that at the plunger is pressed into the syringe a fluid for injection is expelled through the needle. When the injection is complete the plunger is pressed against the end of travel forcing an unlocking device to release the needle from the syringe body and an internal spring to drive the needle into the syringe to prevent reuse. A detent is used to provide tactile feedback so that the plunger is not pressed too far into the syringe while filling it, thereby avoiding premature needle retraction.

It is the primary object of the invention to provide a hypodermic syringe which can be used only one time. A further object of the invention is to provide a hypodermic syringe which absolutely prevents the possibility of accidental scratches from the needle point after the syringe has been used.

A still further object of the invention is to provide a hypodermic syringe which achieves the above without requiring any additional act on the part of the user other than the injection procedure itself. An additional goal of the invention is to provide a hypodermic syringe which automatically withdraws the needle very quickly at the end of the injection thereby lessening the pain of needle withdrawal. These, together with the various ancillary objects and features of the invention which will become apparent as the following description proceeds, are attained by the invention herein shown and described, preferred embodiments thereof being shown in the accompanying drawings, by way of example only.

DESCRIPTION OF THE DRAWINGS

FIG. 2 is a half cross sectional view of the invention showing plunger assembly partly withdrawn from syringe body which contains an injection fluid.

FIG. 3 is a half cross sectional view of the invention showing plunger assembly in the fully inserted position, injection fluid expelled.

FIG. 4 is a half cross sectional view of the invention showing plunger assembly in the fully inserted position, shaft means with injection needle drawn into the plunger.

FIG. 5 is a view of the housing means taken generally on line 5 of FIG. 4, illustrating the location of the guideways for entry and exit of the needle support.

FIG. 6 is a cross sectional view of the unlocking means taken generally on line 6 of FIG. 4, but with needle support means not shown, illustrating the location of the unlocking ears.

FIG. 7 is a view of the needle support means taken generally on line 7 of FIG. 4, but with unlocking means not shown, illustrating the location of the locking ears and unlocking guideways.

DETAILED DESCRIPTION OF THE PREFERRED EMBODIMENT

Figure 1:
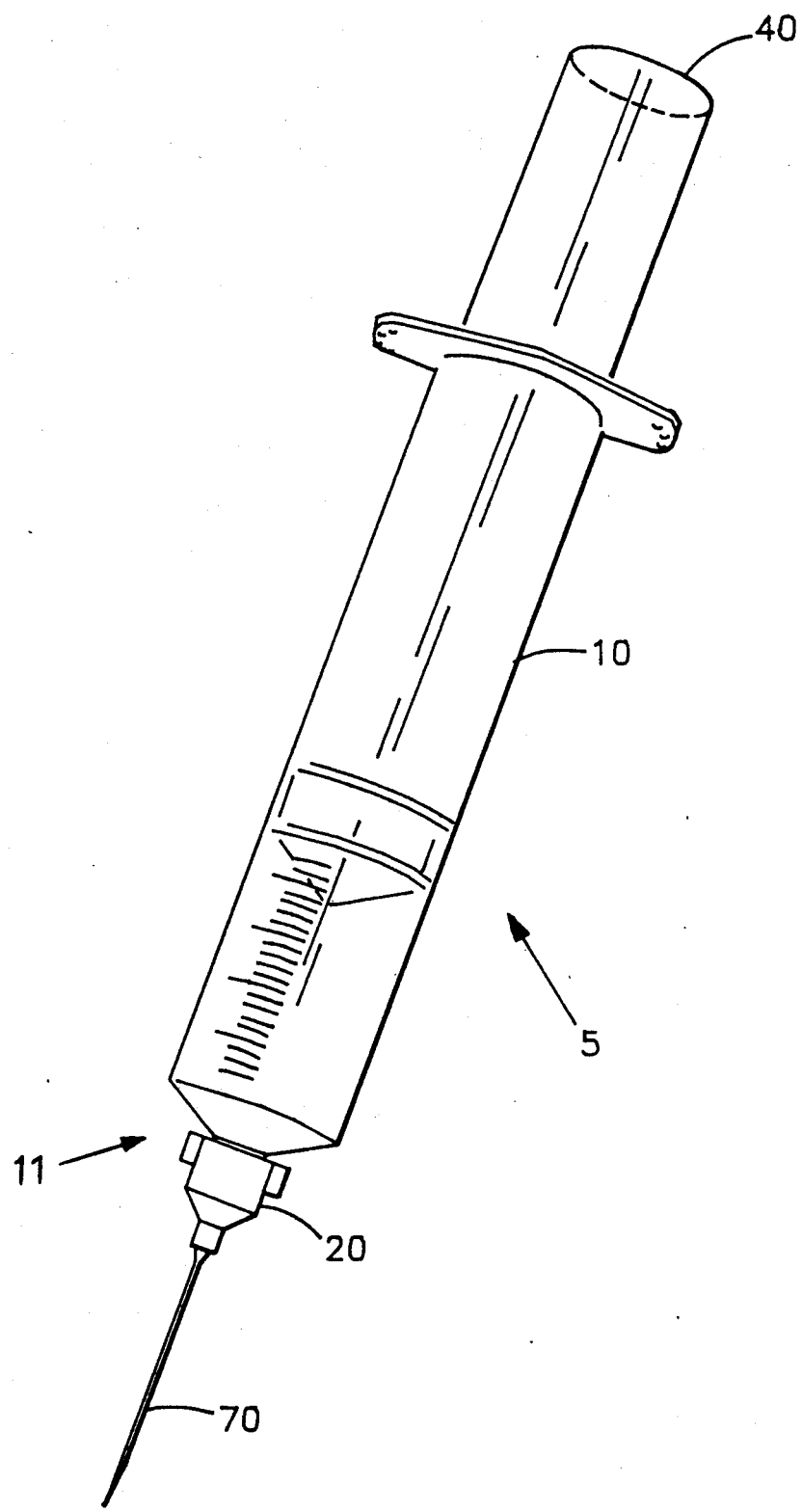
FIG. 1 is a perspective drawing of the invention showing hypodermic syringe with needle assembly mounted at one end and plunger assembly inserted from the opposite end.

As shown in FIGS. 1 through 7 the invention is a self retracting hypodermic syringe 5 which comprises tubular syringe body 10 having injection end 11 supporting outside diameter mounting surface 80 and unlatching means 90. Needle assembly 30 comprises injection needle 70 fixed to needle base 50. Needle base 50 having peripheral locking ears 60 and internal unlocking channels 145. Holding means 20 has internal locking flanges 62, access channels 65 and inside diameter surface mounting means 68. Injecting needle 70 is axially fixed to base 50 while base 50 is, in turn, mounted to holding means 20 in a locked position wherein locking ears 60 are rotated behind locking flanges 62. Holding means 20 is attached by friction to mounting surface 80. Cylindrical plunger assembly 40 comprises elongated plunger 200 having sealing end 112 and driven end 190. Annular sealing means 110 is mounted on sealing end 112. Elongated cylindrical actuation means 170 has unlocking end 115 supporting unlocking ears 140 protruding radially, and retaining end 160 and peripheral latch means 130 protruding radially and peripheral groove 132. Actuation means 170 is mounted coaxially with, and protrudes part way through sealing means 110, however latch means 130 prevents actuation means 170 from passing completely through sealing means 110. Coiled actuation spring 150 is mounted on actuation means 170 and is held compressed between sealing means 110 and retaining end 160. Plunger assembly 40 is constrained within syringe body 10 to linear motion with unlocking end 115 facing needle assembly 30. Sealing means 110 forms a tight sliding seal against body inside diameter 120 and a tight static seal against actuation means 170 forming air tight chamber 111 for holding injection fluid 230, whereby for completing an injection, driven end 190 of plunger assembly 40 is manually pressed into syringe body 10 ejecting injection fluid 230 from injection needle 70 until unlocking end 115 of plunger assembly 40 is pressed against needle assembly 30 forcing unlocking ears 140 into access channel 65 causing base 50 to rotate into an unlocked position wherein locking ears 60 are not obstructed by locking flanges 62 within holding means 20, and locking unlocking ears 140 within access channel 65 for rigid attachment of base 50 to actuation means 170 and forcing unlatching means 90 to contact and unlatch latch means 130 by pressing latch means 130 into groove 132, thereby allowing actuation means 170 to pass through sealing means 110, driven by the expansion force of actuation spring 150 thereby retracting needle 70 into syringe body 10. Internal detent means 100 within syringe body 10 at injection end 11 and sealing end 112 of sealing means 110 cooperate to enable filling syringe 5 without false actuation of the retraction mechanism whereby for filling syringe 5, plunger assembly 40 is pressed into syringe body 10 no further than to just make contact between sealing means 110 and detent means 100. For injection, plunger assembly 40 is pressed inward until sealing means depression 105 is driven into full contact with detent means 100, thereby positioning plunger assembly 40 to cause needle withdrawal actuation.

I claim:

1. A self retracting hypodermic syringe comprising; a tubular syringe body having an injection end supporting an unlatching means; a needle assembly mounted in a locked position on said injection end; a plunger assembly comprising an elongated plunger having a sealing end and a driven end, an annular sealing means mounted on said sealing end, an elongated actuation means having an unlocking end, a retaining end, and a latch means, said actuation means being mounted within said sealing means with said latch means preventing said actuating means from passing through said sealing means, an actuation spring held compressed between said sealing means and said retaining end, said plunger assembly held movably within said syringe body with said unlocking end facing said needle assembly, said sealing means forming a tight sliding seal with said syringe body and a tight static seal against said actuation means forming an air tight chamber for holding an injection fluid, whereby for completing an injection, said driven end of said plunger assembly is manually driven into said syringe body ejecting said injection fluid from said needle assembly until said unlocking end of said plunger assembly is pressed against said injection end of said syringe body forcing said needle assembly into an unlocked position, locking said needle assembly to said actuation means, and forcing said unlatching means to contact and unlatch said latch means thereby allowing said actuation means from fully passing through said sealing means, driven by the expansion force of said actuation spring thereby retracting said needle assembly into said syringe body.

2. A self retracting hypodermic syringe comprising; a tubular syringe body having an injection end supporting a mounting surface and an unlatching means; a needle assembly comprising an injection needle, a needle base and a holding means, said injection needle being fixed to said base, said base being mounted in said holding means in a locked position, said holding means being attached to said mounting surface; a plunger assembly comprising an elongated plunger having a sealing end and a driven end, an annular sealing means mounted on said sealing end, an elongated cylindrical actuation means having an unlocking end, a retaining end and a latch means, said actuation means being mounted coaxially with, and protruding part way through said sealing means, said latch means preventing said actuation means from passing completely through said sealing means, a coiled actuation spring mounted on said actuation means and held compressed between said sealing means and said retaining ends; said plunger assembly held movably within said syringe body with said unlocking end facing said needle assembly, said sealing means forming a tight sliding seal with said syringe body and a tight static seal against said actuation means forming an air tight chamber for holding an injection fluid, whereby for completing an injection, said driven end of said plunger assembly is manually pressed into said syringe body ejecting said injection fluid from said needle assembly until said unlocking end of said plunger assembly is pressed against said needle assembly, forcing said needle base to rotate into an unlocked position within said holding means, locking said base to said actuation means, and forcing said unlatching means to contact and unlatch said latch means thereby allowing said actuation means from fully passing through said sealing means, driven by the expansion force of said actuation spring thereby retracting said needle into said syringe body.

3. A self retracting hypodermic syringe comprising; a tubular syringe body having an injection end supporting an outside diameter mounting surface and an unlatching means; a needle assembly comprising an injection needle fixed to a needle base said base having peripheral locking ears and internal unlocking channels, and a holding means having internal locking flanges, access channels and an inside diameter surface mounting means, said injection needle being axially fixed to said base, said base being mounted in said holding means in a locked position wherein said locking ears are rotated behind said locking flanges, said holding means being held by friction to said mounting surface by said surface mounting means; a cylindrical plunger assembly comprising an elongated plunger having a sealing end and a driven end, an annular sealing means mounted on said sealing end, an elongated cylindrical actuation means having an unlocking end, said unlocking end having unlocking ears protruding radially, a retaining end, a peripheral latch means protruding radially, and a peripheral groove, said actuation means being mounted coaxially with, and protruding part way through said sealing means, said latch means preventing said actuation means from passing completely through said sealing means, a coiled actuation spring mounted on said actuation means and held compressed between said sealing means and said retaining ends; said plunger assembly held movably within said syringe body with said unlocking end facing said needle assembly, said sealing means forming a tight sliding seal with said syringe body and a tight static seal against said actuation means forming an air tight chamber for holding an injection fluid, whereby for completing an injection, said driven end of said plunger assembly is manually pressed into said syringe body ejecting said injection fluid from said needle assembly until said unlocking end of said plunger assembly is pressed against said needle assembly, forcing said unlocking ears into said unlocking channel causing said base to rotate into an unlocked position wherein said locking ears are not obstructed by said locking flanges within said holding means, and locking said unlocking ears within said unlocking channel for rigid attachment of said base to said actuation means, and forcing said unlatching means to contact and unlatch said latch means by pressing said latch means into said groove, thereby allowing said actuation means to fully pass through said sealing means, driven by the expansion force of said actuation spring thereby retracting said needle into said syringe body.

4. The hypodermic syringe of claim 1 or claim 2 or claim 3 further comprising an internal detent means within said syringe body at said injection end and a depression in said sealing means, said depression having a complementary shape to said rim, whereby for filling said syringe, said plunger assembly is pressed into said syringe body no futher than to just make contact between said sealing means and said detent means, while for injecting said fluid, said plunger assembly is pressed into said syringe body until said sealing means depression is driven into full contact with said detent means thereby positioning said plunger assembly to causing needle withdrawal actuation, said detent means providing tactile feedback for avoiding unwanted needle withdrawal actuation while filling said syringe.

* * * * *